United States Patent
Nakamura et al.

(10) Patent No.: US 8,344,733 B2
(45) Date of Patent: Jan. 1, 2013

(54) SAMPLE MEASUREMENT DEVICE, SAMPLE MEASUREMENT SYSTEM AND SAMPLE MEASUREMENT METHOD

(75) Inventors: Toshifumi Nakamura, Ehime (JP); Teppei Shinno, Ehime (JP)

(73) Assignee: Panasonic Corporation, Osaka (JP)

( * ) Notice: Subject to any disclaimer, the term of this patent is extended or adjusted under 35 U.S.C. 154(b) by 399 days.

(21) Appl. No.: 12/812,109

(22) PCT Filed: Mar. 27, 2009

(86) PCT No.: PCT/JP2009/001429
§ 371 (c)(1),
(2), (4) Date: Jul. 8, 2010

(87) PCT Pub. No.: WO2009/119118
PCT Pub. Date: Oct. 1, 2009

(65) Prior Publication Data
US 2010/0283488 A1 Nov. 11, 2010

(30) Foreign Application Priority Data
Mar. 27, 2008 (JP) .................. 2008-082813

(51) Int. Cl.
*G01R 31/08* (2006.01)

(52) U.S. Cl. .......... 324/532; 422/82.01; 422/82.12; 422/68.1; 205/777; 435/286.1; 435/287.1; 204/403.01; 204/403.04; 73/61.61

(58) Field of Classification Search .......... 324/532
See application file for complete search history.

(56) References Cited

U.S. PATENT DOCUMENTS

| | | | | |
|---|---|---|---|---|
| 5,366,609 A | * | 11/1994 | White et al. | 204/403.04 |
| 5,405,511 A | * | 4/1995 | White et al. | 205/777.5 |
| 6,780,296 B1 | * | 8/2004 | Bhullar et al. | 204/403.01 |
| 7,510,643 B2 | | 3/2009 | Bhullar et al. | |
| 7,655,456 B2 | * | 2/2010 | Oshiman et al. | 435/287.1 |

(Continued)

FOREIGN PATENT DOCUMENTS

EP 0 746 762 12/1996
(Continued)

OTHER PUBLICATIONS

International Search Report issued Jun. 2, 2009 in International (PCT) Application No. PCT/JP2009/001429.

*Primary Examiner* — Melissa Koval
*Assistant Examiner* — Benjamin M Baldridge
(74) *Attorney, Agent, or Firm* — Wenderoth, Lind & Ponack, L.L.P.

(57) ABSTRACT

A sample measurement device (110), in which a biosensor (30) having an electrode is mounted, voltage is applied to the electrode, and the concentration of a specific component in a sample deposited on the biosensor (30) is measured, comprises a voltage source (19) configured to apply voltage to the electrode, a time measurement component (22), and a controller (18) configured to control the voltage to be applied and measure the concentration of the specific component. The time measurement component (22) measures a detection time, which is the length of time between the mounting of the biosensor (30) and the deposition of a sample on the biosensor (30). The controller (18) changes a set value for measuring the concentration of a specific component according to the detection time. Consequently, measurement accuracy can be improved regardless of the temperature of the biosensor (30).

22 Claims, 9 Drawing Sheets

U.S. PATENT DOCUMENTS

| | | | |
|---|---|---|---|
| 8,121,857 B2* | 2/2012 | Galasso et al. | 705/2 |
| 2002/0037238 A1* | 3/2002 | Haar et al. | 422/68.1 |
| 2003/0159945 A1* | 8/2003 | Miyazaki et al. | 205/777.5 |
| 2003/0203498 A1 | 10/2003 | Neel et al. | |
| 2004/0094432 A1 | 5/2004 | Neel et al. | |
| 2004/0094433 A1 | 5/2004 | Neel et al. | |
| 2004/0099540 A1 | 5/2004 | Neel et al. | |
| 2004/0104131 A1 | 6/2004 | Neel et al. | |
| 2004/0182703 A1* | 9/2004 | Bell et al. | 204/403.11 |
| 2004/0216516 A1* | 11/2004 | Sato | 73/64.56 |
| 2004/0238357 A1* | 12/2004 | Bhullar et al. | 204/400 |
| 2005/0019219 A1* | 1/2005 | Oshiman et al. | 422/82.12 |
| 2005/0045476 A1 | 3/2005 | Neel et al. | |
| 2006/0156796 A1* | 7/2006 | Burke et al. | 73/61.44 |
| 2007/0089987 A1 | 4/2007 | Neel et al. | |
| 2008/0098802 A1* | 5/2008 | Burke et al. | 73/61.61 |
| 2008/0112852 A1* | 5/2008 | Neel et al. | 422/82.01 |
| 2008/0201169 A1* | 8/2008 | Galasso et al. | 705/2 |
| 2008/0297169 A1* | 12/2008 | Greenquist et al. | 324/600 |
| 2009/0236237 A1* | 9/2009 | Shinno et al. | 205/792 |
| 2010/0283488 A1 | 11/2010 | Nakamura et al. | |
| 2010/0327886 A1* | 12/2010 | Nakamura et al. | 324/692 |
| 2011/0198241 A1* | 8/2011 | Murakami | 205/792 |
| 2012/0103806 A1* | 5/2012 | Shinno et al. | 204/403.01 |
| 2012/0132540 A1* | 5/2012 | Wang et al. | 205/775 |

FOREIGN PATENT DOCUMENTS

| | | |
|---|---|---|
| EP | 1 491 882 | 12/2004 |
| EP | 1 504 252 | 2/2005 |
| EP | 1 709 187 | 10/2006 |
| EP | 2 040 065 | 3/2009 |
| JP | 8-502590 | 3/1996 |
| JP | 8-503304 | 4/1996 |
| JP | 2001-235444 | 8/2001 |
| JP | 2003-42995 | 2/2003 |
| JP | 2007-33459 | 2/2007 |
| JP | 2007-522449 | 8/2007 |
| WO | 94/29703 | 12/1994 |
| WO | 94/29704 | 12/1994 |
| WO | 03/062812 | 7/2003 |
| WO | 03/091717 | 11/2003 |
| WO | 2008/004565 | 1/2008 |
| WO | 2009/119118 | 10/2009 |

* cited by examiner

|  | 15°C | 20°C | 25°C | 30°C |
|---|---|---|---|---|
| T = 1.0 | 1.8 | 2.4 | 2.6 | 2.0 |
| T = 3.0 | 1.6 | 2.1 | 2.3 | 1.7 |
| T = 5.0 | 1.4 | 1.8 | 2.0 | 1.4 |
| T = 10.0 | 0.8 | 1.0 | 1.1 | 0.8 |
| T = 15.0 | 0.2 | 0.2 | 0.3 | 0.2 |

(seconds)

|  | 15°C | 20°C | 25°C | 30°C |
|---|---|---|---|---|
| T = 1.0 | 0.14 | 0.19 | 0.20 | 0.15 |
| T = 3.0 | 0.12 | 0.16 | 0.18 | 0.13 |
| T = 5.0 | 0.11 | 0.14 | 0.15 | 0.11 |
| T = 10.0 | 0.06 | 0.08 | 0.09 | 0.06 |
| T = 15.0 | 0.02 | 0.02 | 0.02 | 0.02 |

(seconds)

SAMPLE MEASUREMENT DEVICE, SAMPLE MEASUREMENT SYSTEM AND SAMPLE MEASUREMENT METHOD

TECHNICAL FIELD

The present invention relates to a sample measurement device, a sample measurement system, and a sample measurement method, with which a biosensor is used to quantify a specific component in a sample.

BACKGROUND ART

A biosensor is a sensor in which an ability to recognize the molecules of a biological material, such as microbes, enzymes, or antibodies, is utilized, and a biological material is used as a molecular labeling element. Specifically, a fixed biological material makes use of a reaction that occurs when a targeted specific component is recognized, the consumption of oxygen by the respiration of microbes, an enzyme reaction, light emission, and so forth. In particular, biosensors that make use of enzyme reactions have seen considerable practical application, and are used in the medical and food preparation fields.

An example of a biosensor measuring system that makes use of an enzyme reaction will now be described through reference to FIGS. 12 and 13.

Figure 12:
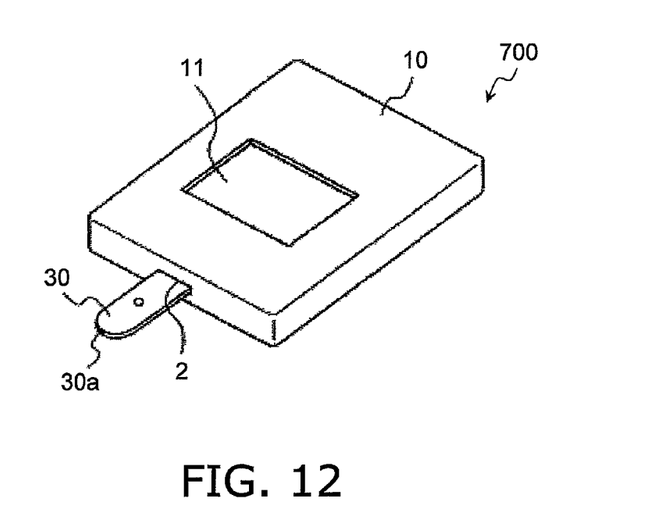
FIG. 12 is an oblique view of an example of a conventional biosensor measurement system.

The biosensor measuring system 700 in FIG. 12 comprises a biosensor 30 having at its distal end a sample deposition component 30a, and a measuring device 10 for measuring the concentration of a specific component in a liquid sample deposited on the sample deposition component 30a.

The measuring device 10 comprises a support component 2 for mounting the biosensor 30, and a display component 11 for displaying the measurement results.

Figure 13:
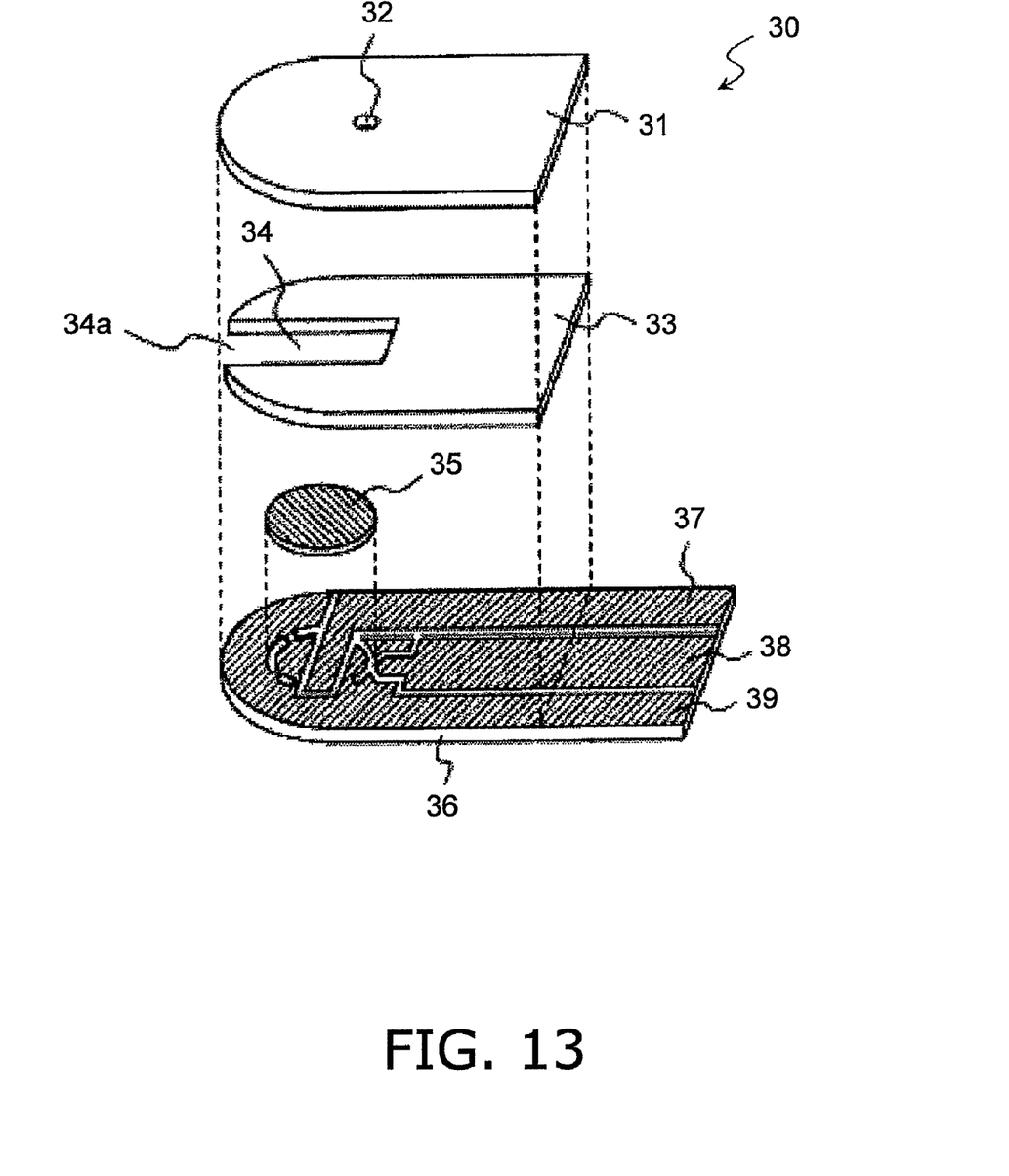
FIG. 13 is an exploded oblique view of an example of the configuration of a conventional biosensor.

An example of the above-mentioned biosensor 30 is shown in FIG. 13. The biosensor in FIG. 13 is made up of a cover 31, a spacer 33, a reagent layer 35, and an insulated substrate 36, all of which are laminated.

The cover 31 has an air hole 32 in its center.

The spacer 33 has a substantially rectangular sample supply path 34. The sample supply path 34 is open at one end, forming a sample supply port 34a.

The reagent layer 35 supports a reagent that undergoes an enzyme reaction with a specific component in a liquid sample.

The insulated substrate 36 is composed of polyethylene terephthalate or another such material, and has an electrode layer formed on its surface. The electrode layer is divided up with a laser or the like to form a working electrode 37, a detecting electrode 38, and a counter electrode 39.

Next, the method used by the biosensor measuring system 700 to measure a liquid sample will be described. Here, a case of measuring the glucose concentration in blood will be described.

As shown in FIG. 12, when the biosensor 30 is inserted into the support component 2 of the measuring device 10, a constant voltage is applied between the working electrode 37 and the counter electrode 39.

To describe this in further detail, a specific voltage is applied between the detecting electrode 38 and the working electrode 37 at the point when the biosensor 30 has been inserted into the support component 2 of the measuring device 10. In this state, when blood is deposited in the sample supply port 34a of the biosensor 30, the blood seeps along the sample supply path 34 by capillary action, goes past the working electrode 37 and the counter electrode 39, and reaches the detecting electrode 38, whereupon current (also called response current) flows between the detecting electrode 38 and the working electrode 37. That is, detecting a change in the current value allows detection that the blood has reached all the way to the detecting electrode 38, which is the electrode disposed farthest along the sample supply path 34.

At the stage when the blood has reached the reagent layer 35, the reagent layer 35 dissolves, and the glucose in the blood and the reagent held in the reagent layer 35 bring about an enzyme reduction reaction. When a specific voltage is applied between the working electrode 37 and the counter electrode 39 in this state, a current change value between the working electrode 37 and the counter electrode 39 (hereinafter also referred to as response current) is detected. The glucose concentration in the blood is calculated on the basis of the current change value thus detected, and this calculation result is displayed by the display component 11 of the measuring device 10.

However, because an enzyme reaction is highly temperature dependent, temperature changes during measurement, etc., can cause measurement accuracy to suffer.

Various ways to improve measurement accuracy are known. With one biosensor measurement system, a temperature correction table that shows the relation between glucose concentration and temperature correction amounts is prepared ahead of time, and this temperature correction table is used to provide a temperature correction algorithm for correcting the measurement results according to the environment temperature during measurement (see Patent Citation 1, for example).

Another known biosensor measurement system for improving measurement accuracy involves providing a thermal conduction layer over the insulated substrate 36 of the biosensor 30, measuring the temperature of the biosensor itself, and correcting the measurement result on the basis of the temperature of the biosensor itself (see Patent Citations 2 and 3, for example). Yet another known biosensor measurement system involves providing a temperature detector to the support component 2 of the measuring device 10, measuring the temperature of the biosensor 30 by bringing the temperature detector into contact when the biosensor 30 is mounted, and correcting the measurement result on the basis of the detected temperature (see Patent Citation 4, for example).

Patent Citation 1: Published Japanese Translation No. 8-503304 of the PCT International Publication
Patent Citation 2: Japanese Laid-Open Patent Application 2001-235444
Patent Citation 3: Japanese Laid-Open Patent Application 2003-42995
Patent. Citation 4: International Laid-Open Patent Application 03/062812

DISCLOSURE OF INVENTION

Technical Problem

The temperature correction algorithm used in the conventional biosensor measurement system disclosed in Patent Citation 1 does not measure the actual sample temperature, but rather measures the environment temperature around the measuring device, and this value is considered to be the sample temperature in the measurement of the specimen. However, the biosensors most often used today are handled by the bare hands of the user. Therefore, heat from the user's fingers may be conducted to the biosensor, where it may locally change the temperature, creating a difference between the actual sample temperature and the temperature of the surroundings. In particular, with a self-monitoring blood glucose measurement system aimed at diabetic patients, the user grasps the sensor directly by hand for insertion into the measuring device.

These self-monitoring blood glucose measurement sensors have been getting smaller in recent years. Nearly all self-monitoring blood glucose measurement sensors have a structure with which the user's hand touches the area around the reagent reaction part during insertion into the measuring device. When measurement of a specimen is begun in this state, the sample temperature is different from the surrounding environment temperature read by a thermistor of the measuring device, so the proper correction processing cannot be effected. As a result, the measured value ends up deviating greatly from the true value. Such problems are particularly apt to be encountered when specimen measurement is to be performed as soon as the biosensor is mounted to the measuring device, such as when a nurse or operator measures a patient's specimen, or when a parent of a diabetic child is assisting in the measurement.

With the biosensor measurement system proposed in Patent Citations 2 and 3, the temperature of the biosensor can be ascertained, but a thermistor has to be provided to the biosensor itself. Therefore, with such a system the biosensor is more expensive, and its use as a disposable biosensor is impractical. Furthermore, since the biosensor relies on temperature measurement by means of a heat conduction layer, its reproducibility is poor, and measurement takes a long time.

Also, with the biosensor measurement system proposed in Patent Citation 4, since a temperature detector has to be provided to the measuring device, in addition to the extra cost, there is the risk that measurement accuracy will be low, particularly when the measurement lasts a short time.

Further, with today's biosensor measurement systems, there is a tendency toward shorter measurement times. For instance, in the measurement of blood glucose level, the measurement is over about 5 seconds after the blood is deposited on the sensor. Accordingly, the measurement result is greatly affected not only by the surrounding environment temperature, but also by the temperature of the actual reaction component. Therefore, there has been a need for a biosensor measurement system with higher measurement accuracy.

The present invention was conceived in order to solve the above-mentioned problems, and it is an object thereof to provide a sample measurement device, a sample measurement system, and a sample measurement method with which measurement error can be reduced.

Technical Solution

To solve the above-mentioned problems, the sample measurement device pertaining to a first aspect of the invention is a sample measurement device in which a biosensor having an electrode is mounted, voltage is applied to the electrode, and the concentration of a specific component in a sample deposited on the biosensor is measured, said device comprising a voltage source configured to apply voltage to the electrode, a time measurement component, and a controller configured to control the voltage that is applied and measure the concentration of the specific component. With this sample measurement device, the time measurement component measures a detection time, which is the length of time from the mounting of the biosensor until the sample is deposited on the biosensor. The controller changes a set value for measuring the concentration of the specific component according to the detection time.

The "set value for measuring the concentration of the specific component" here is the value of a measurement parameter predetermined according to the type of sample, the specific component, etc., examples of which include a measurement time and an applied voltage. To change the set value, for example, it can be changed by referring to a table, or it may be calculated from a specific formula on the basis of the detection time.

The above-mentioned sample measurement device, despite its simple configuration, prevents the temperature of the sensor itself from affecting the measurement result when the concentration of a specific component in a sample is measured. Consequently, even with a short detection time until the sample is deposited on the biosensor, a highly accurate measurement result can be obtained with little measurement error.

The sample measurement device pertaining to a second aspect of the invention is the sample measurement device of the first aspect, wherein the set value is a measurement time for measuring the concentration of the specific component.

The sample measurement device pertaining to a third aspect of the invention is the sample measurement device of the second aspect, wherein the shorter is the detection time, the more the controller extends the measurement time.

The sample measurement device pertaining to a fourth aspect of the invention is the sample measurement device of the first aspect, wherein the set value is a value of the voltage applied to the electrode.

The sample measurement device pertaining to a fifth aspect of the invention is the sample measurement device of the first aspect, wherein the controller determines whether or not the detection time is within a specific length of time, and changes the set value when it is determined that the detection time is within the specific length of time.

The sample measurement device pertaining to a sixth aspect of the invention is the sample measurement device of the first aspect, further comprising a temperature measurement component configured to measure an environment temperature, wherein the controller further changes the set value according to the measured environment temperature.

The environment temperature referred to here is the temperature surrounding the measuring device.

The sample measurement device pertaining to a seventh aspect of the invention is the sample measurement device of the first aspect, further comprising a hematocrit value calculation unit, wherein the controller further changes the set value according to the hematocrit value calculated by the hematocrit value calculation unit.

The sample measurement device pertaining to an eighth aspect of the invention is the sample measurement device of the first aspect, wherein there are a plurality of set values, and the plurality of set values are a measurement time for measuring the concentration of the specific component, and a value of the voltage applied to the electrode, respectively.

The sample measurement device pertaining to a ninth aspect of the invention is the sample measurement device of the first aspect, wherein the controller sets the set value according to a type of sample.

Setting the set value here includes changing the predetermined parameter according to the type of sample, the specific component, etc., and changing the parameter setting range. For example, a set value corresponding to the type of sample may be set by changing the reference table or by changing the mathematical formula.

The sample measurement device pertaining to a tenth aspect of the invention is the sample measurement device of the first aspect, wherein there are a plurality of specific components, and the controller changes the set values for the concentrations of the plurality of specific components, respectively.

The sample measurement system pertaining to an eleventh aspect of the invention comprises the sample measurement device to the first aspect, and a biosensor that is mounted to the sample measurement device.

The sample measurement system pertaining to a twelfth aspect of the invention is the sample measurement system of the eleventh aspect, wherein there are a plurality of biosensors, and the sample measurement device measures the concentrations of a plurality of types of specific components.

The sample measurement system pertaining to a thirteenth aspect of the invention is the sample measurement system of the eleventh aspect, wherein there are a plurality of biosensors, and the sample measurement device measures the concentration of one type of specific component.

The sample measurement method pertaining to a fourteenth aspect of the invention is a method in which a biosensor having an electrode is mounted to a measuring device for measuring the concentration of a specific component in a sample, voltage is applied to the electrode, and the concentration of a specific component in a sample deposited on the biosensor is measured, said method comprising measuring a detection time, which is the length of time between the mounting of the biosensor to the measuring device and the deposition of the sample on the biosensor; changing a set value for measuring the concentration of the specific component, according to the detection time; and measuring the concentration of the specific component on the basis of the set value.

The above-mentioned sample measurement method prevents the temperature of the sensor itself from affecting the measurement result when the concentration of a specific component in a sample is being measured. Consequently, even with a short detection time until the sample is deposited on the biosensor, a highly accurate measurement result can be obtained with little measurement error.

The sample measurement method pertaining to a fifteenth aspect of the invention is the sample measurement method of the fourteenth aspect, wherein the set value is a measurement time for measuring the concentration of the specific component.

The sample measurement method pertaining to a sixteenth aspect of the invention is the sample measurement method of the fifteenth aspect, wherein, in said changing the set value, the shorter is the detection time, the more the measurement time is extended.

The sample measurement method pertaining to a seventeenth aspect of the invention is the sample measurement method of the fourteenth aspect, wherein the set value is a value of the voltage applied to the electrode.

The sample measurement method pertaining to an eighteenth aspect of the invention is the sample measurement method of the fourteenth aspect, wherein said changing the set value further includes determining whether or not the detection time is within a specific length of time, and changing the set value when it is determined that the detection time is within the specific length of time.

The sample measurement method pertaining to a nineteenth aspect of the invention is the sample measurement method of the fourteenth aspect, further comprising measuring an environment temperature, wherein the set value is changed according to the environment temperature in said changing the set value.

The sample measurement method pertaining to a twentieth aspect of the invention is the sample measurement method of the fourteenth aspect, further comprising calculating a hematocrit value, wherein, in said changing the set value, the set value is changed according to the hematocrit value calculated in said calculating the hematocrit value.

The sample measurement method pertaining to a twenty-first aspect of the invention is the sample measurement method of the fourteenth aspect, wherein there are a plurality of set values, and the plurality of set values are a measurement time for measuring the concentration of the specific component, and a value of the voltage applied to the electrode, respectively.

The sample measurement method pertaining to a twenty-second aspect of the invention is the sample measurement method of the fourteenth aspect, further comprising setting the set value according to a type of sample.

Advantageous Effects

The present invention provides a sample measurement device, a sample measurement system, and a sample measurement method with which measurement error can be reduced.

EXPLANATION OF REFERENCE

100 biosensor measurement system (sample measurement system)

2 support component
10, 110 measuring device (sample measurement device)
11 display component
12, 13, 14 connector
15 switching circuit
16 current/voltage conversion circuit
17 A/D conversion circuit
18 CPU (controller)
19 reference voltage source (voltage source)
20 temperature sensor (temperature measurement component)
21 memory
22 timer (time measurement component)
30 biosensor
30a sample deposition component
31 cover
32 air hole
33 spacer
34 sample supply path
34a sample supply port
35 reagent layer
36 insulated substrate
37 working electrode
38 detecting electrode
39 counter electrode
700 biosensor measuring system

BEST MODE FOR CARRYING OUT THE INVENTION

Embodiments of the present invention will now be described through reference to the drawings.

1. Embodiment 1

A biosensor measurement system (sample measurement system) 100 pertaining to Embodiment 1 of the present invention will now be described. Blood is used here as the specimen (sample). The specific component to be measured is the glucose concentration.

1.1 Biosensor Measurement System 100

Figure 1:
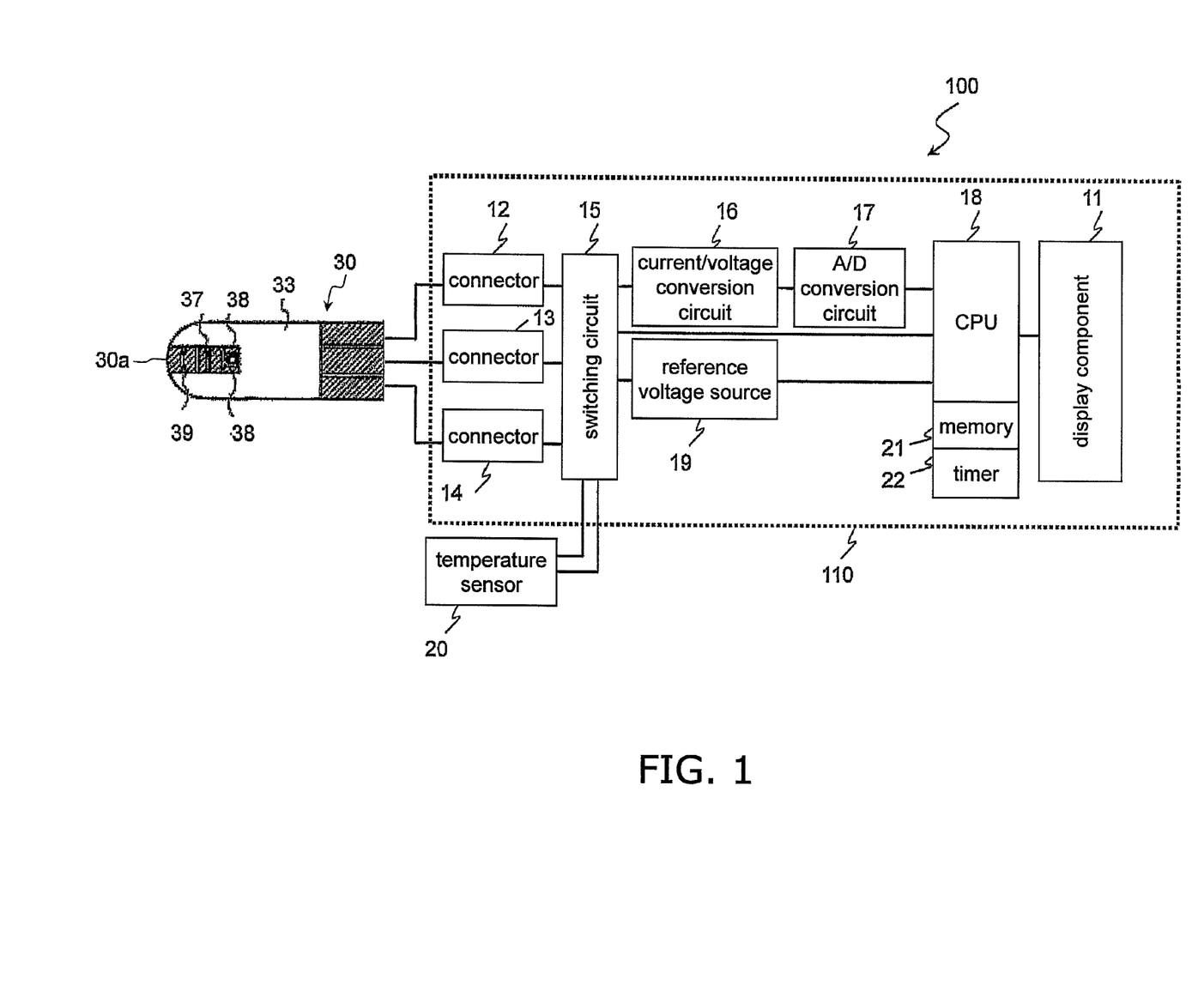
FIG. 1 is a constitution diagram of a biosensor measurement system in Embodiment 1 of the present invention.

FIG. 1 is a simplified diagram of the constitution of the biosensor measurement system 100 in Embodiment 1. Those components that are the same as in the biosensor measuring system 700 in FIG. 12 are numbered the same in FIG. 1.

The biosensor measurement system 100 of Embodiment 1 comprises a biosensor 30 and a measuring device (sample measurement device) 110. The biosensor 30 is held directly in the hand of the user, and is mounted in the measuring device 110 to perform measurement. The configuration of the biosensor 30 is the same as that shown in FIG. 13, and will not be described again here.

1.2 Measuring Device 110

1.2.1 Configuration of Measuring Device 110

The measuring device 110 comprises a display component 11, connectors 12, 13, and 14, a switching circuit 15, a current/voltage conversion circuit 16, an A/D conversion circuit 17, a CPU (controller) 18, a reference voltage source (voltage source) 19, a temperature sensor (temperature measurement component) 20, a memory 21, and a timer (time measurement component) 22.

The connectors 12, 13, and 14 are in contact with the working electrode 37, the detecting electrode 38, and the counter electrode 39, respectively, of the mounted biosensor 30.

The switching circuit 15 switches the connection between the reference voltage source 19 and the connectors 12 to 14, and the connection between the current/voltage conversion circuit 16 and the connectors 12 to 14.

The current/voltage conversion circuit 16 converts the current flowing between the working electrode 37 and the other electrodes 38 and 39 into voltage.

The A/D conversion circuit 17 converts the output value from the current/voltage conversion circuit 16 into a pulse.

The CPU 18 calculates the concentration of a specific component in a specimen on the basis of the pulse from the A/D conversion circuit 17. The CPU 18 also outputs a specific control signal to control the switching circuit 15 and the application of voltage by the reference voltage source 19.

The reference voltage source 19 applies voltage between the connectors 12 to 14.

The temperature sensor 20 consists of a thermistor or the like, and measures the environment temperature around the measuring device 110. The measured data is sent to the CPU at a specific timing via a specific bus (not shown). Preferably, the temperature sensor 20 is provided near the support component 2 of the biosensor 30, inside the measuring device 110. This allows the temperature close to the specimen to be detected accurately. The optimal correction value is selected from a temperature correction table (not shown) stored ahead of time in the memory of the measuring device 110, on the basis of the environment temperature detected by the temperature sensor 20, and is corrected with respect to the value that is the measurement result for specimen concentration.

The timer 22 counts the time T from when the biosensor 30 is mounted to the support component 2 until it is detected that blood (the specimen) has been deposited on the biosensor 30 (hereinafter referred to as the detection time).

The memory 21 stores a temperature correction table (not shown), a table for changing the measurement time (discussed below; a set value for measuring), and so forth. The temperature correction table is used to determine the amount of correction of the measurement result for the concentration of a specific component in a specimen deposited on the biosensor 30, on the basis of the environment temperature. The memory 21 may be, for example, a flash memory or another ROM.

1.2.2 Operation of Measuring Device 110

With the measuring device 110 pertaining to Embodiment 1, measurement error produced by finger heat on the biosensor 30 is reduced when the detection time T is shorter, so the measurement time (the set value for measuring) is changed according to the detection time T. The operation of the measuring device 110 pertaining to Embodiment 1 will now be described, while touching on how it differs from a conventional measuring device.

Operation of Conventional Measuring Device

Figure 2:
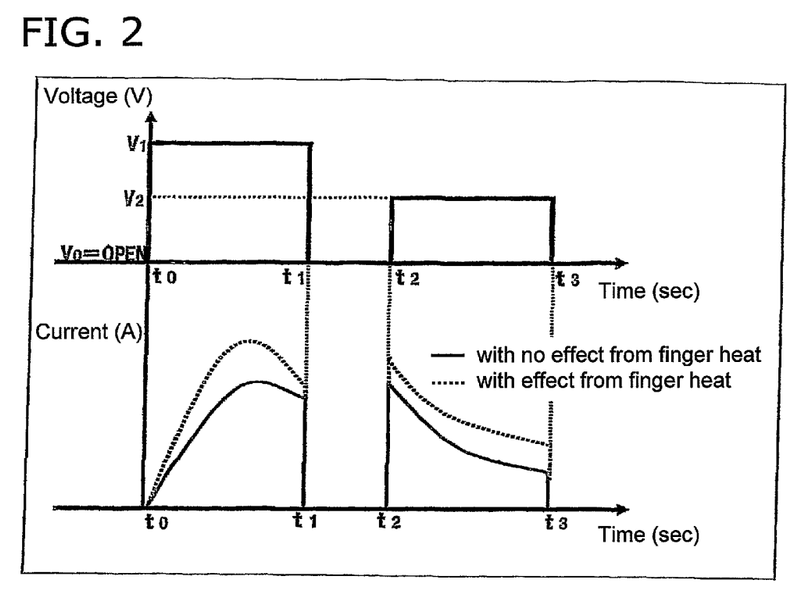
FIG. 2 is a graph of the measurement profile with a conventional biosensor measurement system, and the response current curve thus obtained.

FIG. 2 is a graph of the measurement profile with a conventional measurement method, and the current response curve obtained by this measurement method.

In the profile diagram shown at the top in FIG. 2, the vertical axis is the applied voltage (V) for measuring, and the horizontal axis is the measurement time t (seconds). With the current response curves shown at the bottom in FIG. 2, the vertical axis is the current response curve i (A), and the horizontal axis is the measurement time t (seconds).

The profile in FIG. 2 consists of three steps.

The first step is from t0 to t1, letting t0 between the time at which it is first detected that blood has been supplied. In the first step, a voltage V1 is applied for preprocessing the supplied blood. The second step is from t1 to t2. In the second step, we will assume an open circuit (0 V). The third step is from t2 to t3. In the third step, a voltage V2 is applied to oxidize a reducing electron carrier produced after a specific length of time has elapsed.

With a conventional measurement method, the first step involves applying a voltage of 0.60 V for 2 seconds, the second step involves opening the circuit for 1 second, and the third step involves applying a voltage of 0.40 V for 2 seconds. Therefore, a total measurement time of approximately 5 seconds is entailed. With the current response curve thus obtained (FIG. 2), compared to ordinary measurement in which there is no effect of finger heat (shown by a solid line), measurement in which there is the effect of finger heat (dotted line) can be seen to give a higher response current. Here, "ordinary measurement," that is, "measurement in which there is no effect of finger heat," refers to a case in which measurement is begun in a state in which there is no effect of finger heat on the biosensor 30 because the detection time T is long. Meanwhile, "measurement in which there is the effect of finger heat" refers to a case in which measurement is begun in a state in which finger heat has been transferred to the biosensor 30 because the detection time T is short. In the case of measurement in which there is the effect of finger heat, the response current is higher, and the measurement value after approximately 5 seconds (at the end of measurement) is a higher value.

The conventional biosensor measuring system 700 subjects the measurement result for glucose concentration in blood deposited on the biosensor 30 to temperature correction using a temperature correction table that has been stored in advance. The temperature correction table indicates the amount of correction based on the environment temperature and the glucose concentration. However, with the conventional biosensor measuring system 700, the following problems were encountered according to the time until the start of measurement.

Figure 3:
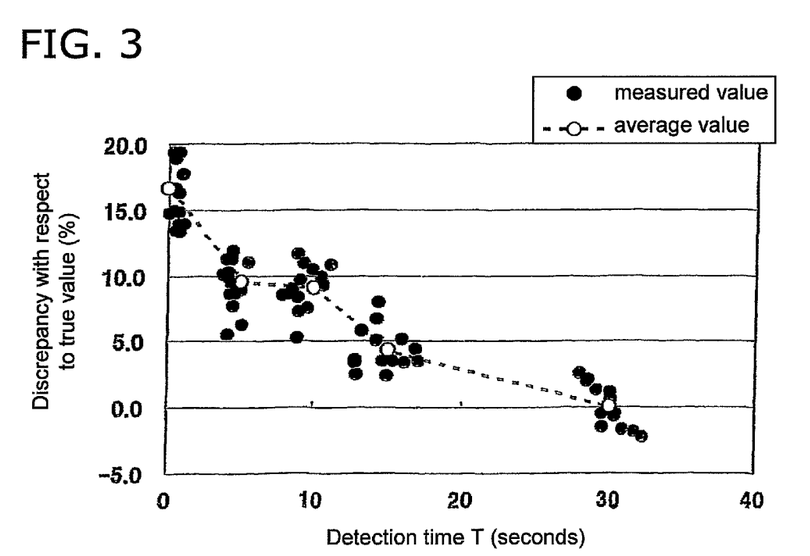
FIG. 3 is a graph of the relation between the detection time T and the discrepancy from the true value when measurement is performed using a conventional biosensor measurement system.

FIG. 3 shows the measurement results obtained with the conventional biosensor measuring system 700. The horizontal axis shows the detection time T (seconds) from the mounting of the biosensor 30 to the measuring device 10 until blood is deposited on the biosensor 30, while the vertical axis shows the discrepancy (%) from the true value with respect to the measurement value. Here, measurement was performed using a specimen adjusted to a glucose concentration of 100 mg/dL (hematocrit value of 45%), at an environment temperature of 25° C. Six donors with different finger temperatures were used here, the biosensor 30 was mounted to the measuring device 10, and measurement was performed with the detection time T from the mounting of the biosensor 30 until a specimen was deposited being set between 0.01 and 30 seconds.

As can be seen from FIG. 3, the shorter is the detection time T, the greater the discrepancy from the true value. That is, finger heat seems to affect the measurement result.

Operation of Measuring Device 110 of Embodiment 1

In contrast, with the biosensor measurement system 100 pertaining to Embodiment 1 of the present invention, the length of time the glucose concentration in blood deposited on the biosensor 30 was measured was changed on the basis of the detection time T from the mounting of the biosensor 30 to the measuring device 110 until blood was deposited on the biosensor 30.

Figure 4:
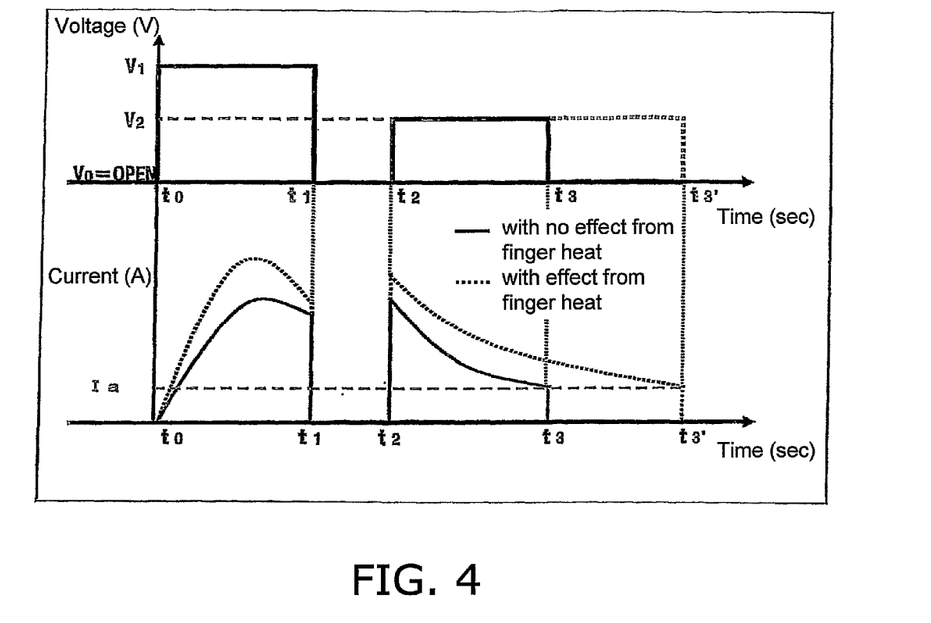
FIG. 4 is a graph of the measurement profile with the biosensor measurement system of Embodiment 1, and the response current curve thus obtained.

FIG. 4 is a graph of the profile of the measurement method in Embodiment 1, and the current response curve obtained with this measurement method.

With the biosensor measurement system 100 pertaining to Embodiment 1, the profile differs from a conventional profile in that the length of time that the voltage V2 is applied in the third step is extend from t3 to t3'. This voltage V2 is applied to oxidize the reducing electron carrier that is produced. Thus extending how long the voltage is applied reduces the effect that finger heat has on the measurement result. Specifically, the measurement time is extended so that the current value Ia (FIG. 4) will be the same as that in ordinary measurement (solid line) in which there is no effect of finger heat, even when the detection time T is short and measurement is begun in a state in which finger heat has been transmitted to the biosensor 30 (indicated by the dotted line). The response current value (Ia in FIG. 4) at the completion of application of this voltage V2 is converted into a glucose concentration.

Correction of the measurement time of glucose concentration in the blood is determined on the basis of the discrepancy from the true value. For instance, if the detection time T is 1.0 second, it can be seen from FIG. 3 that the discrepancy from the true value is +16%, so when the glucose concentration at a temperature of 25° C. is 100 mg/dL, the measurement time of 5 seconds is extended by 2.6 seconds so that the discrepancy from the true value will be 0%. Specifically, t3' is 7.6 seconds. If the detection time T is 5.0 seconds, the measurement time of 5 seconds is extended by 2.0 seconds. Specifically, t3' becomes 7.0 seconds. Furthermore, if the detection time T is 15.0 seconds, the measurement time of 5 seconds is extended by 0.3 second, so that t3' is 5.3 seconds.

Figure 5:
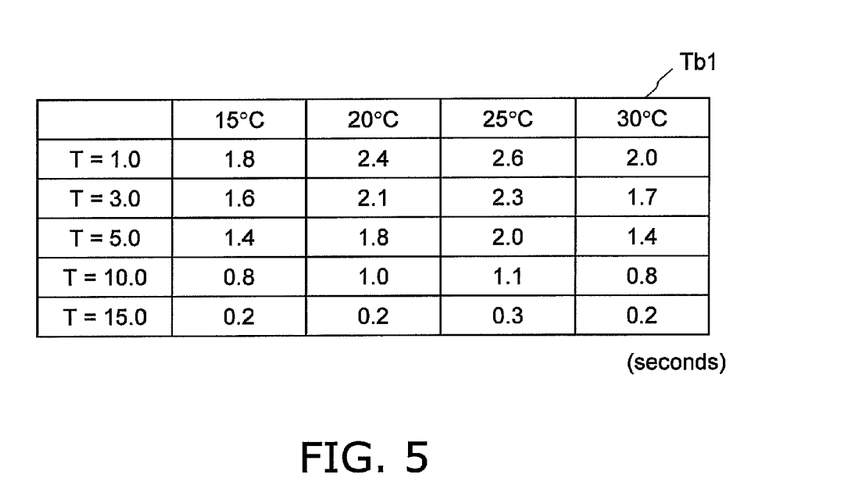
FIG. 5 is a table listing examples of the amount of measurement time extension in the biosensor measurement system of Embodiment 1.

The amount of correction of these measurement times is determined by referring to a measurement time extension table Tb1 held in a memory, etc., as shown in FIG. 5. The measurement time extension table Tb1 shown in FIG. 5 is a table listing the amount of extension of the measurement time versus the detection time T, and the numerical values indicate extension times in seconds. The vertical axis is the detection time T (seconds), and the horizontal axis is the measured environment temperature.

Thus, with the measuring device 110 pertaining to Embodiment 1, the measurement time is corrected according to the environment temperature and the detection time T, which changes the method for measuring the concentration of a specific component in a specimen deposited on the biosensor 30.

Rather than measuring the environment temperature, the measurement time may also be corrected according to the detection time T alone.

That is, in the past, measurement was always performed using a specific measurement time, regardless of the detection time T, but with Embodiment 1, the measurement time is extended according to the detection time T.

Furthermore, in Embodiment 1, as shown in FIG. 4, the discussion was of a case of extending t3 to t3', but other cases are also possible. For example, t1 in the first step may be extended, or t2 in the second step may be extended. Also, it is possible to provide a time t0' from the time t0 at which blood was detected until the start of the first step, and the same effect will be obtained.

Figure 6:
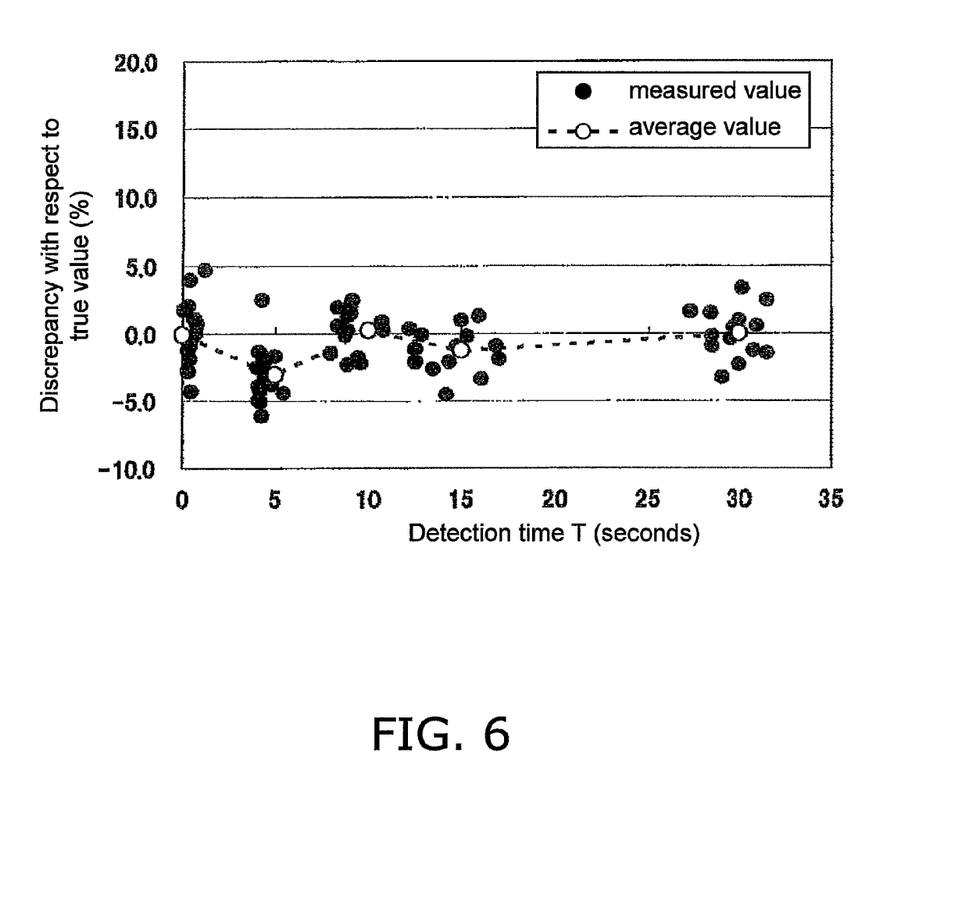
FIG. 6 is a graph of the relation between detection time T and the discrepancy from the true value with respect to the measured value when measurement is performed using the biosensor measurement system of Embodiment 1.

Thus, with the measuring device 110 pertaining to Embodiment 1, the measurement time is extended according to the detection time T, with respect to the measurement of glucose concentration in blood that has been deposited on the biosensor 30. Consequently, as shown in FIG. 6, even if the detection time T is 20 seconds or less, discrepancy from the true value with respect to the measurement value can be kept to a minimum, and measurement accuracy can be increased.

Also, with the biosensor measurement system 100 of this embodiment, as shown in FIG. 5, the measured environment temperature is added as a parameter, rather than using just the detection time T until the deposition of blood. This is because the effect that finger heat has on a measurement result will vary with the measured environment temperature. Consequently, measurement accuracy can be dramatically increased.

The measurement time extension table Tb1 in FIG. 5 was discussed as a table related to the detection time T and the measured environment temperature, but other options are also possible. Measurement at even higher accuracy can be achieved with the measurement time extension table Tb1 by using as parameters those factors that are affected by finger heat, such as the hematocrit value of blood.

The measurement time when using the measurement time extension table Tb1 shown in FIG. 5 is extended by the following method.

For example, when the environment temperature is 25° C. and the detection time T is 1.0 second, it can be seen from FIG. 5 that the measurement time is extended by 2.6 seconds. It can also be seen that when the time T is 5.0 seconds, the measurement time is extended by 2.0 seconds, and when the time T is 15.0 seconds, the measurement time is extended by 0.3 second.

Also, when the time T is 2.0 seconds, the measurement extension time when T=1.0 second (2.6 seconds) and the measurement extension time when T=3.0 seconds (2.3 seconds) are subjected to linear regression to calculate the measurement extension time when T=2.0 seconds as 2.45 seconds.

The numerical values shown in FIG. 5 are just examples, and the present invention is not limited to these. Nor is the number of tables limited to what is given here, and the more tables there are, the better the measurement accuracy will be.

1.2.3 Operation Processing of Measuring Device 110

Figure 7:
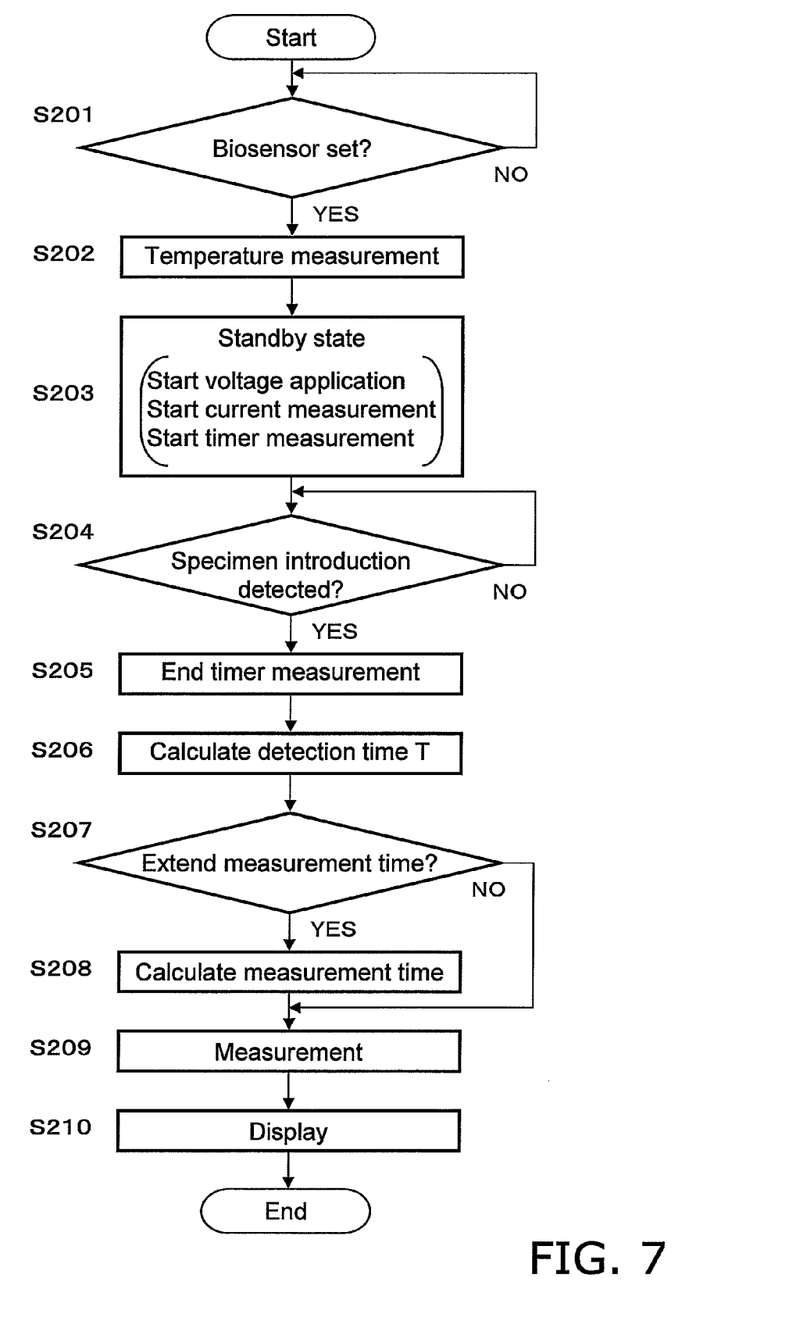
FIG. 7 is a flowchart of sample measurement processing with the biosensor measurement system of Embodiment 1.

Next, the flow of processing for measuring a specimen with the measuring device 110 in Embodiment 1 will be described through reference to FIG. 7.

Step S201

First, the biosensor 30 is placed in the support component 2 of the measuring device 110. At this point the CPU 18 determines from a switch inside the support component 2 whether or not the biosensor 30 has been inserted. If the biosensor 30 has been inserted, the power to the biosensor measurement system 100 is automatically switched on. Voltage is applied to the connectors 12 to 14 from the reference voltage source 19 inside the measuring device 110. This makes it possible to detect whether or not the biosensor 30 is a specific type.

Step 202 (Temperature Measurement Step)

The environment temperature is then measured by the temperature sensor 20.

Step S203

The measuring device 110 enters a specimen introduction standby state.

The "specimen introduction standby state" refers to a state in which a constant voltage is applied between the detecting electrode 38 and the working electrode 37 by applying a constant voltage from the reference voltage source 19 to the connectors 12 to 14 in accordance with the CPU 18's command. At this point current measurement by the current/voltage conversion circuit 16 is begun, and measurement of the detection time T from the mounting of the biosensor 30 until a specimen is deposited on the biosensor 30 is begun by the timer 22.

The sequence and timing of the various processing in steps S202 and S203 are not limited to those given above.

In step S201, a case was described in which power to the measuring device 110 was automatically switched on by insertion of the biosensor 30 into the support component 2, but the power to the measuring device 110 may instead be switched on manually. Here again, it is determined whether or not the biosensor 30 has been inserted, and the system enters a specimen introduction standby state.

Step S204

When blood (a specimen) is deposited on the biosensor 30, the CPU 18 reads a change in the current value via the current/voltage conversion circuit 16 and the A/D conversion circuit 17. Consequently, it is detected that a specimen has been introduced to (deposited on) the biosensor 30.

Step S205

Upon receiving the detection of specimen introduction in step S204, the CPU 18 ends the counting of the timer 22.

Step S206 (Time Measurement Step)

The CPU 18 calculates the detection time T.

Step S207

The CPU 18 decides whether or not to extend the measurement time on the basis of the detection time T calculated in step S206. This decision processing will be discussed in detail below.

Step S208 (Set Value Change Step)

Next, if it has been decided in step S207 to extend the measurement time, the CPU 18 refers to the measurement time extension table Tb1 and calculates the extended measurement time.

On the other hand, if it has been decided in step S207 not to extend the measurement time, the CPU 18 proceeds to step S209.

Step S209 (Measurement Step)

The CPU 18 performs according to the calculated measurement time, and calculates the glucose concentration in the blood deposited on the biosensor 30. At this point, the amount of correction is found from the temperature correction table held in the memory 21 on the basis of the environment temperature measured in step S202, and the measurement result for glucose concentration in the blood deposited on the biosensor 30 is corrected.

Step S210

The glucose concentration measured and calculated in step S209 is displayed on the display component 11. The configuration may be such that if it is decided from the detection time T that the measurement result has poor reliability, the measurement result is not displayed, and an error display is performed instead, or the display may indicate that the reliability of the measurement result is low.

1.2.4 Decision Processing for Extension of Measurement Time

The decision processing as to whether or not to extend the measurement time may be preset if various parameters are within the ranges given below, for example.

If the detection time T is within a range of from 0.01 to 60 seconds, the measurement time is to be changed. Preferably, the measurement time is changed if the detection time T is between 0.01 and 30 seconds, and even more preferably if it is between 0.01 and 20 seconds. As to the interval at which the detection time T is read, measurements may be made every second. Preferably, measurements are made every 0.1 second, and more preferably every 0.01 second.

If the environment temperature is within a range of from 5 and 45° C., the measurement time is to be changed. Preferably, the measurement time is changed if the environment temperature is from 10 to 40° C., and even more preferably if it is from 15 to 35° C.

If the hematocrit value (Hct %) can be measured ahead of time, then the measurement time is to be changed when the Hct is within a range of from 0 to 70%. Preferably, the measurement time is to be changed when the Hct is within a range of from 20 to 70%, and even more preferably when the Hct is within a range of from 40 to 70%.

The hematocrit value is calculated, for example, by providing another working electrode (hematocrit electrode) besides the working electrode 37, and applying voltage to this electrode (hematocrit value calculation unit, hematocrit value calculation step).

In Embodiment 1, a measurement value of higher reliability can be obtained by performing the above processing.

2. Embodiment 2

The biosensor measurement system (sample measurement system) 100 pertaining to Embodiment 2 of the present invention will now be described.

Those components that are the same as in Embodiment 1 will be numbered the same. Also, since the constitution of the biosensor measurement system and the measuring device is the same as that in Embodiment 1, it will not be described in detail again here.

2.1 Operation of Measuring Device 110

The measuring device 110 pertaining to Embodiment 2 (FIG. 1) differs from that in Embodiment 1 in that the applied voltage value for measuring (the set value for measuring) is changed on the basis of the detection time T from the mounting of the biosensor 30 to the measuring device 110 until the biosensor 30 detects that a specimen has been deposited.

Figure 8:
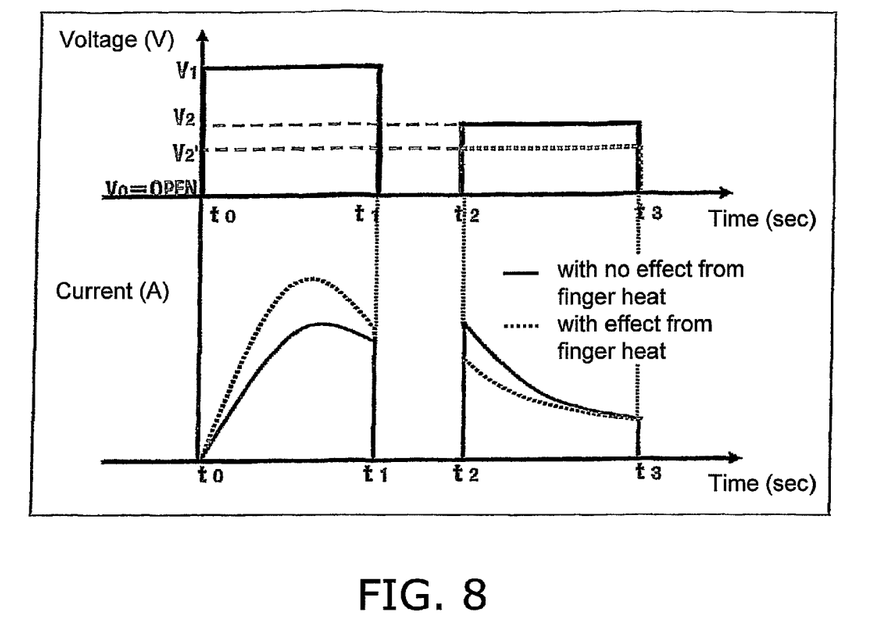
FIG. 8 is a graph of the measurement profile with the biosensor measurement system of Embodiment 2, and the response current curve thus obtained.

FIG. 8 is a graph of the measurement profile in Embodiment 2, and the current response curve thus obtained. In this embodiment, in the third step the voltage V2 is lowered to V2'. The voltage V2 is applied to oxidize a reducing electron carrier produced after a specific length of time has elapsed. Lowering the voltage V2 to V2' mitigates the effect that finger heat has on the measurement result. Specifically, the applied voltage is lowered so that the current value will be the same as that in ordinary measurement (solid line) in which there is no effect of finger heat, even when the detection time T is short and measurement is begun in a state in which finger heat has been transmitted to the biosensor.

Correction of the voltage value for measuring the glucose concentration in blood is determined on the basis of the discrepancy from the true value. For instance, if the detection time T is 1.0 second, it can be seen from FIG. 3 that the discrepancy from the true value is +16%. Accordingly, when the environment temperature is 25° C., the applied voltage is reduced by 0.20 V so that the discrepancy from the true value will be 0%. If the detection time T is 5.0 seconds, the applied voltage is reduced by 0.15 V, and if the detection time T is 15.0 seconds, the applied voltage is reduced by 0.02 V. This improves the measurement accuracy.

In other words, the voltage value applied for measuring is changed on the basis of the detection time T in this embodiment.

Furthermore, in this embodiment a case was discussed in which V2 was lowered to V2' as shown in FIG. 8, but the present invention is not limited to this. For instance, the same effect can be anticipated when V1 is changed.

Figure 9:
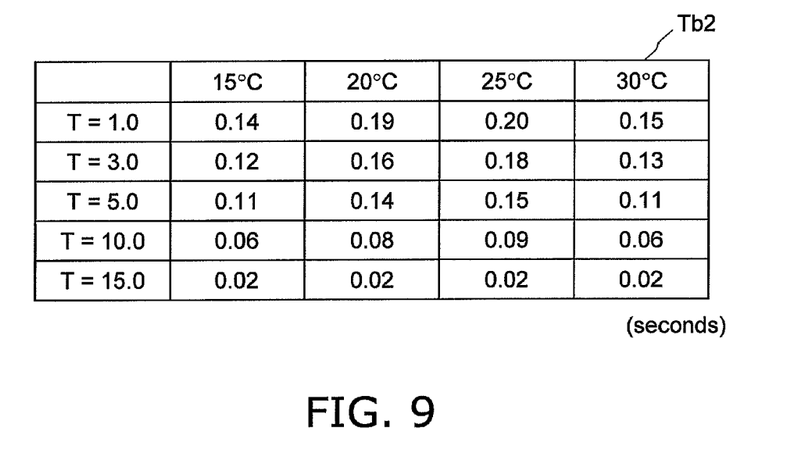
FIG. 9 is a table listing examples of the amount of change in the applied voltage in the biosensor measurement system of Embodiment 2.

FIG. 9 shows an applied voltage change table Tb2 showing change values for the detection time T and applied voltage. The numerical values indicate the amount of reduction (V) in the applied voltage. The vertical axis is the detection time T, and the horizontal axis is the environment temperature. The numerical values shown in FIG. 9 are just examples, and the present invention is not limited to these. Nor is the number of tables limited to what is given here, and the more tables there are, the better the measurement accuracy will be.

Next, the method for changing the applied voltage will be described in detail, for when the applied voltage change table Tb2 shown in FIG. 9 is used.

For example, when the environment temperature is 25° C. and the detection time T is 1.0 second, the applied voltage is reduced by 0.20 V on the basis of the applied voltage change table Tb2 in FIG. 9. When the detection time T is 5.0 seconds, the applied voltage is reduced by 0.15 V, and when the detection time T is 15.0 seconds, the applied voltage is reduced by 0.02 V.

If the detection time T is 2.0 seconds, the amount of decrease in applied voltage when T=1.0 second (0.20 V) and the amount of decrease in applied voltage when T=3.0 seconds (0.18 V) are subjected to linear regression. Consequently, the applied voltage when T=2.0 seconds is reduced by 0.19 V.

2.2 Operation Processing of Measuring Device 110

Figure 10:
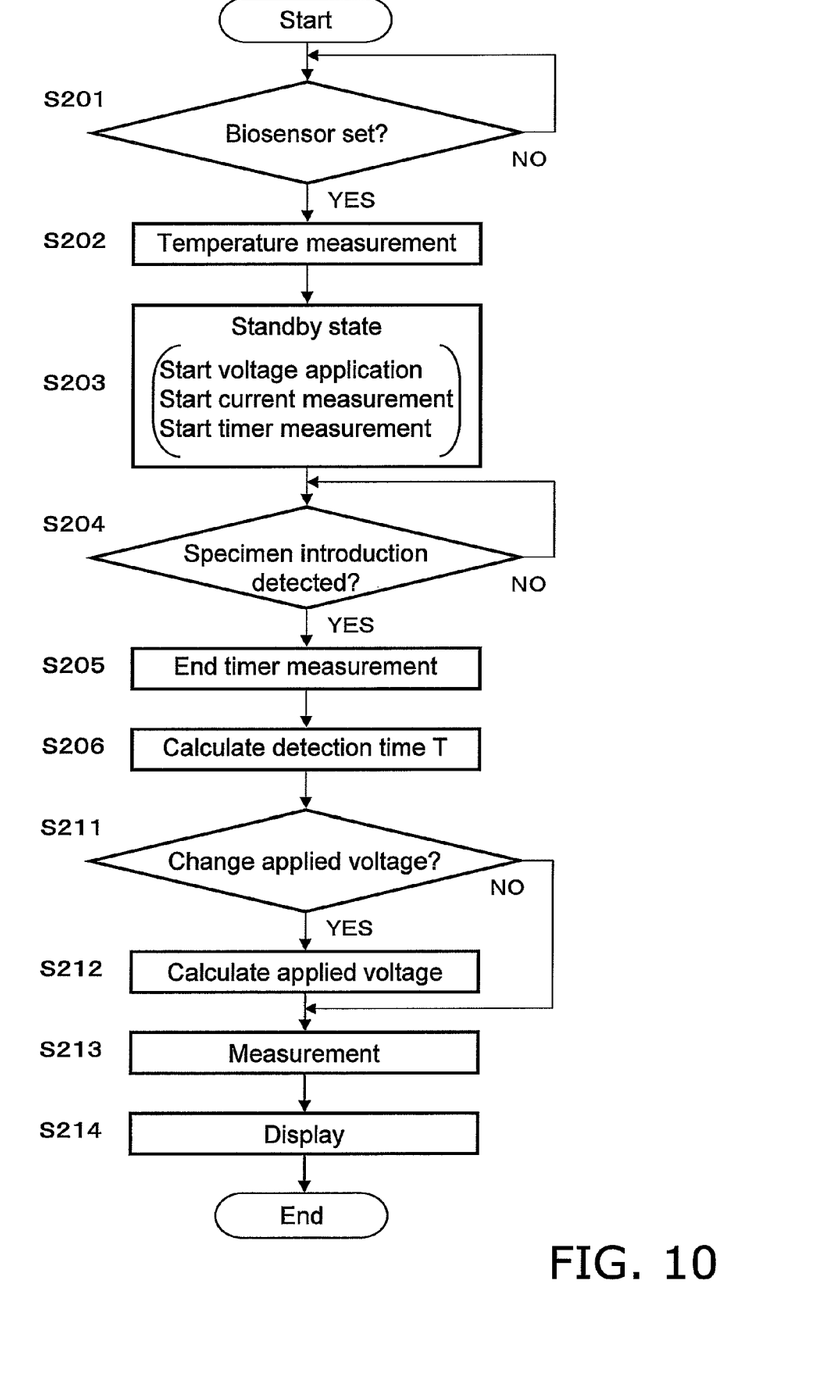
FIG. 10 is a flowchart of a sample measurement processing method with the biosensor measurement system of Embodiment 2.

Next, the flow of processing for measuring a specimen with the measuring device 110 in this embodiment will be described through reference to FIG. 10. In FIG. 10, the processing up to the calculation of the detection time T, from the mounting of the biosensor 30 to the support component 2 of the measuring device 110 until specimen introduction is detected (steps S201 to S206), is the same as in Embodiment 1 above (FIG. 7), so it will not be described again here.

Step S211

The CPU 18 decides whether or not to change the applied voltage for measuring, on the basis of the detection time T up until specimen introduction is detected (step S206). This decision processing will be discussed in detail below.

Step S212 (Set Value Change Step)

If it has been decided in step S211 to change the applied voltage, the CPU 18 refers to the applied voltage change table Tb2 shown in FIG. 9 and calculates the voltage to be applied.

On the other hand, if it has been decided in step S211 not to change the applied voltage, the CPU 18 proceeds to step S213.

Step S213 (Measurement Step)

After this, the CPU 18 performs measurement using the calculated applied voltage, and calculates the glucose concentration in the blood deposited on the biosensor 30. At this point the CPU 18 finds the amount of correction from a temperature correction table (not shown) held in the memory 21 based on the environment temperature measured in step S202, and performs correction on the measurement result for the glucose concentration of blood deposited on the biosensor 30.

Step S214

In step S213, the measured glucose concentration is displayed on the display component 11. If it is decided from the detection time T that the reliability of the measurement result is poor, the measurement result is not displayed, and an error display is performed instead, or the display may indicate that the reliability of the measurement result is low.

2.3 Decision Processing for Changing Applied Voltage

The decision processing as to whether or not to change the applied voltage is preset if various parameters are within the ranges given below, for example.

If the detection time T is within a range of from 0.01 to 60 seconds, the applied voltage is to be changed. Preferably, the applied voltage is changed if the detection time T is between 0.01 and 30 seconds, and even more preferably if it is between 0.01 and 20 seconds.

As to the interval at which the detection time T is read, measurements are made every second. Preferably, measurements are made every 0.1 second, and more preferably every 0.01 second.

If the environment temperature is within a range of from 5 and 45° C., the applied voltage is to be changed. Preferably, the applied voltage is changed if the environment temperature is from 10 to 40° C., and even more preferably if it is from 15 to 35° C.

If the hematocrit value (Hct %) can be measured ahead of time, then the applied voltage is to be changed when the Hct is within a range of from 0 to 70%. Preferably, the applied voltage is to be changed if the Hct is within a range of from 20 to 70%, and even more preferably when the Hct is within a range of from 40 to 70%.

The hematocrit value is calculated, for example, by providing another working electrode (hematocrit electrode) besides the working electrode 37, and applying voltage to this electrode (hematocrit value calculation unit, hematocrit value calculation step).

Figure 11:
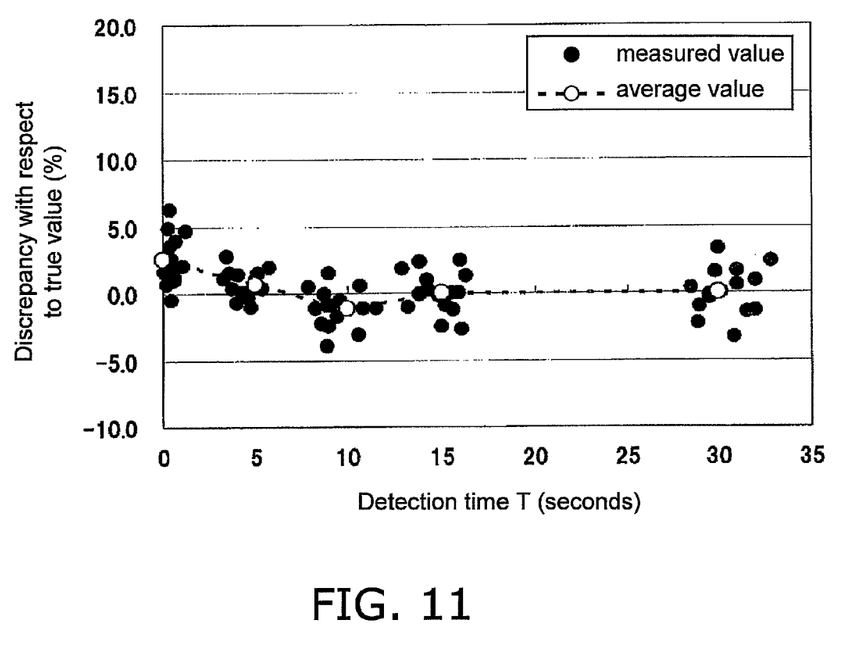
FIG. 11 is a graph of the relation between the detection time T and the discrepancy from the true value with respect to the measured value with the biosensor measurement system of Embodiment 2.

Thus, if the applied voltage V2 for measuring is reduced when measuring the glucose concentration of blood deposited on the biosensor 30, on the basis of the detection time T, then as shown in FIG. 11, even if the detection time T is 20 seconds or less, discrepancy from the true value with respect to the measurement value can be kept to a minimum, and measurement accuracy can be increased.

The result of the above operation is that a value with higher reliability can be obtained.

3. Effect of Embodiments

With the measuring device 110 and the measurement method pertaining to Embodiments 1 and 2 above, the detection time T from the mounting of the biosensor 30 to the measuring device 110 until blood is deposited on the biosensor 30 is measured, and the set value (measurement time or applied voltage) for measuring the glucose concentration of blood deposited on the biosensor 30 is changed. Consequently, finger heat is prevented from affecting the measurement result, and an accurate measurement result can be obtained even when the detection time T is short. Also, no new temperature sensor has to be provided for measuring the temperature of the biosensor 30 itself, so an accurate measuring device 110 can be achieved at a low cost and with a simple structure.

4. Modification Examples (1)
In Embodiments 1 and 2 above, the tables Tb1 and Tb2 are referred to in changing the set value (measurement time or applied voltage), but the set value may instead be calculated from a specific mathematical formula according to the detection time T or the measurement temperature.

Also, a calculation formula may be used that makes use of a coefficient or a parameter other than the detection time T or the measurement temperature.

(2)
In Embodiments 1 and 2 above, a case was discussed in which either measurement time or applied voltage is changed in the method for measuring the glucose concentration in blood deposited on the biosensor 30, but the present invention is not limited to this, and the same effect can be anticipated when both measurement time and applied voltage are changed.

(3)
In Embodiments 1 and 2 above, it was decided that no extension of the measurement time was necessary when the detection time T exceeded 20 seconds, but the present invention is not limited to this, and the measurement time may be made longer or shorter depending on what is being measured.

(4)
In Embodiments 1 and 2 above, measurement was performed according to the detection time T in relation to a single kind of specific component in the specimen, but the present invention can also be applied to a case in which the biosensor is capable of measurement in relation to a plurality of kinds of specific components in the specimen. For example, when glucose concentration and lactic acid concentration are measured simultaneously with a single sensor as the specific components in blood, the measurement time may be varied according to the detection time T so as to perform the optimal measurement for each specific component. Consequently, even if the measurement result is different for each specific component being measured because of the effect of finger heat, measurement can be performed that accommodates variance in the extent of this effect.

The number of kinds of components to be measured is not limited to two, and more kinds of components may be used.

(5)
Embodiments 1 and 2 above can also be applied to a case in which a plurality of the same or different kinds of biosensor are inserted into a single measuring device. The measuring device recognizes the type of biosensor from the electrode pattern on the biosensor or the operation of a manual button. If the types of biosensor, the types of deposited sample, or the types of specific components being measured are different, then the same effect can be obtained as long as the set value (measurement time or applied voltage) for measuring the concentration of the specific components is set according to these types depending on the detection time T. The setting of the set value can be accomplished by changing the table that is referenced, by changing the mathematical formula, etc (set value setting step).

The measuring device may measure the concentration of a plurality of types of specific components for a plurality of samples, or may measure a single type of specific component shared by a plurality of samples.

(6)
In Embodiments 1 and 2 above, it is also possible to add glucose concentration, hematocrit value, or the like, rather than using just the detection time T or the environment temperature, as factors that change the method for measuring glucose concentration in blood deposited on the biosensor 30. This will markedly improve measurement accuracy.

(7)
In Embodiments 1 and 2 above, blood glucose described as substance to be measured, but the present invention is not limited to this, and the same effect will be obtained with cholesterol, triglyceride, lactic acid, uric acid, bilirubin, alcohol, and other such biological samples, as well as environmental samples, food samples, and so forth.

INDUSTRIAL APPLICABILITY

The present invention is useful as a sample measurement device that is low in cost and affords good measurement accuracy, for example.

What is claimed is:

1. A sample measurement device, in which a biosensor having an electrode is mounted, voltage is applied to the electrode by the sample measurement device, and the concentration of a specific component in a sample deposited on the biosensor is measured, said sample measurement device comprising:
   a voltage source that applies voltage to the electrode;
   a time measurement component; and a controller that controls the voltage that is applied and that measures the concentration of the specific component, wherein the time measurement component measures a detection time, which is the length of time from the mounting of the biosensor until the sample is deposited on the biosensor, and the controller changes a set value for measuring the concentration of the specific component, according to the detection time.

2. The sample measurement device according to claim 1, wherein the set value is a measurement time for measuring the concentration of the specific component.

3. The sample measurement device according to claim 2, wherein the shorter is the detection time, the more the controller extends the measurement time.

4. The sample measurement device according to claim 1, wherein the set value is a value of the voltage applied to the electrode.

5. The sample measurement device according to claim 1, wherein the controller:

determines whether or not the detection time is within a specified length of time; and changes the set value when it is determined that the detection time is within the specified length of time.

6. The sample measurement device according to claim 1, further comprising a temperature measurement component configured to measure an environment temperature, wherein the controller further changes the set value according to the measured environment temperature.

7. The sample measurement device according to claim 1, further comprising a hematocrit value calculation unit, wherein the controller further changes the set value according to the hematocrit value calculated by the hematocrit value calculation unit.

8. The sample measurement device according to claim 1, wherein the controller chooses a set value from a plurality of set values, and the plurality of set values consist of a measurement time for measuring the concentration of the specific component, and a value of the voltage applied to the electrode.

9. The sample measurement device according to claim 1, wherein the controller sets the set value according to a type of sample.

10. The sample measurement device according to claim 1, wherein there is a plurality of types of specific components in a sample, and the controller changes the set values for the concentrations of the plurality of types of specific components.

11. A sample measurement system, comprising:

the sample measurement device according to claim 1; and a biosensor that is mounted to the sample measurement device.

12. The sample measurement system according to claim 11, wherein the sample measurement system comprises a plurality of biosensors, and the sample measurement device measures the concentrations of a plurality of types of specific components.

13. The sample measurement system according to claim 11, wherein the sample measurement system comprises a plurality of biosensors, and the sample measurement device measures the concentration of one type of specific component.

14. A sample measurement method, in which a biosensor having an electrode is mounted to a measuring device for measuring the concentration of a specific component in a sample, voltage is applied to the electrode by the sample measurement device, and the concentration of the specific component in a sample deposited on the biosensor is measured, said sample measurement method comprising:

measuring a detection time, which is the length of time between the mounting of the biosensor to the measuring device and the deposition of the sample on the biosensor;

changing a set value for measuring the concentration of the specific component, according to the detection time; and measuring the concentration of the specific component on the basis of the set value.

15. The sample measurement method according to claim 14, wherein the set value is a measurement time for measuring the concentration of the specific component.

16. The sample measurement method according to claim 15, wherein, in said changing the set value, the shorter is the detection time, the more the measurement time is extended.

17. The sample measurement method according to claim 14, wherein the set value is a value of the voltage applied to the electrode.

18. The sample measurement method according to claim 14, wherein said changing the set value further includes:

determining whether or not the detection time is within a specified length of time, and changing the set value when it is determined that the detection time is within the specified length of time.

19. The sample measurement method according to claim 14, further comprising measuring an environment temperature, wherein the set value is changed according to the environment temperature in said changing the set value.

20. The sample measurement method according to claim 14, further comprising calculating a hematocrit value, wherein, in said changing the set value, the set value is changed according to the hematocrit value calculated in said calculating the hematocrit value.

21. The sample measurement method according to claim 14, wherein changing the set value comprises choosing from a plurality of set values, and the plurality of set values consist of a measurement time for measuring the concentration of the specific component, and a value of the voltage applied to the electrode.

22. The sample measurement method according to claim 14, further comprising setting the set value according to a type of sample.

* * * * *